(12) United States Patent
Franklin et al.

(10) Patent No.: US 6,410,001 B1
(45) Date of Patent: *Jun. 25, 2002

(54) COSMETIC COMPOSITIONS

(75) Inventors: Kevin Ronald Franklin; Ian Peter Stott, both of Wirral; Rahila Bhat, Nelson, all of (GB)

(73) Assignee: Unilever Home & Personal Care, USA, a division of Conopco, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/620,858

(22) Filed: Jul. 21, 2000

(30) Foreign Application Priority Data

Jul. 23, 1999 (EP) .............................. 99305840

(51) Int. Cl.$^7$ .................. A61K 7/32; A61K 7/34; A61K 7/00
(52) U.S. Cl. ................. 424/65; 424/66; 424/400; 424/401
(58) Field of Search ................. 424/65, 66, 400, 424/401

(56) References Cited

U.S. PATENT DOCUMENTS 4,371,370 A     2/1983   Rose
6,241,976 B1 *  6/2001   Esser et al. .................. 424/65

FOREIGN PATENT DOCUMENTS

DE   30 11 191   10/1981
EP   0512770     11/1992
WO   98/34588    8/1998

OTHER PUBLICATIONS

International Search Report Application No. PCT GB 00/02646 mailed Nov. 8, 2000.
Chemical Abstracts, vol. 79, No. 12, "Manufacture of an Analgesic for Skin Inflammation", p. 255—XP 002128650.

* cited by examiner

Primary Examiner—Shelley A. Dodson
(74) Attorney, Agent, or Firm—Kevin J. Stein

(57) ABSTRACT

Compositions for application to human skin have a continuous phase which contains water-immiscible oil structured by incorporation of a compound of formula

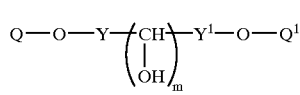

(I)

in which Y and $Y^1$ are each independently —$CH_2$ or >CO Q and $Q^1$ are each independently a hydrocarbyl group of at least 6 carbon atoms and m is from 2 to 4.

The composition may be an antiperspirant containing suspended particulate antiperspirant active or containing a dispersed phase in which antiperspirant active is dissolved in water or water-immiscible solvent.

33 Claims, No Drawings

COSMETIC COMPOSITIONS

FIELD OF THE INVENTION

The present invention relates to cosmetic compositions for application to human skin. The invention can be applied within a range of cosmetic compositions. Significant forms of the invention include deodorant and antiperspirant compositions for application to human skin, especially the axilla.

BACKGROUND OF THE INVENTION AND SUMMARY OF PRIOR ART

A wide variety of cosmetic compositions for application to human skin make use of a thickened or structured liquid which is applied to the surface of the skin. In some compositions such as lip salves, the application of this liquid is directly beneficial. In others, the thickened or structured liquid serves as a carrier to deliver colour or some other active material to the surface of the skin. A significant example of such cosmetic compositions are antiperspirant compositions which are widely used in order to enable their users to avoid or minimise wet patches on their skin, especially in axillary regions.

Antiperspirant formulations have been provided with a range of different product forms. One of these is a so-called "stick" which is usually a bar of an apparently firm solid material held within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact.

Another possibility is that a stick is a softer solid composition accommodated in a dispensing container which in use extrudes the composition through one or more apertures.

These antiperspirant formulations can be divided into three categories. Suspension sticks contain a particulate antiperspirant active material suspended in a structured carrier liquid phase. Emulsion sticks normally have a hydrophilic phase containing the antiperspirant active in solution, this phase forming an emulsion with a second, more hydrophobic, liquid phase. The continuous phase of the emulsion is structured. Solution sticks typically have the antiperspirant active dissolved in a structured liquid phase which may be a mixture of water and a water-miscible organic solvent. This classification into suspension, emulsion and solution types can be applied to both firm and soft solid compositions.

Other types of cosmetic composition can also be provided in the form of a stick or soft solid and again the stick may be a structured solution, emulsion or suspension. Examples of cosmetic compositions which are, or can be, marketed in a stick form are deodorants intended to counteract perspiration odour, lipsticks, lip salves and eyebrow pencils.

Compositions which are, or could be, marketed in soft solid or cream form include moisturisers, deodorants and sunscreens.

There is substantial literature on the structuring or thickening of cosmetic compositions.

Conventionally, many sticks have been structured using naturally-occurring or synthetic waxy materials. Examples of these include those fatty alcohols which are solid at room temperature, such as stearyl alcohol, and hydrocarbon waxes or silicone waxes. Such materials are widely available, and by suitable selection of the materials themselves and their concentrations in the formulation, it is possible to obtain either a soft solid or a firm solid. Examples of wax-structured sticks are given in an article in Cosmetics and Toiletries, 1990, Vol 105, pages 75–78 and in U.S. Pat. Nos. 5,169,626 and 4,725,432. However, fatty alcohol structured sticks tend to leave visible white deposits on application to human skin, and the deposits can also transfer onto clothing when it comes into contact with the skin and the wearer can, for example, find white marks at the armhole of the sleeveless garment.

Some alternative structurants have been proposed. The term "gellant" is often employed instead of "structurant". Where the resulting product is liquid of increased viscosity rather than a solid or gel, the term "thickener" can also be used. For example, the use of dibenzylidene sorbitol (DBS) or derivatives thereof as gellant has been proposed in a number of publications such as EP-A-512770, WO 92/19222, U.S. Pat. Nos. 4,954,333, 4,822,602 and 4,725,430. Formulations containing such gellants can suffer from a number of disadvantages, including instability in the presence of acidic antiperspirants, and comparatively high processing temperatures needed in the production of sticks.

A combination of an N-acylaminoacid amide and 12-hydroxy stearic acid to gel a non-aqueous formulation is described in, for example, WO 93/23008 and U.S. Pat. No. 5,429,816. However, high processing temperatures are needed to dissolve the gellants and prevent premature gelling. When applied to skin the formulation can be difficult to wash off, but reformulation to overcome that problem can be made impossible by the need for a high processing temperature.

The use of 12-hydroxy stearic acid without N-acylamidoacid amide as a secondary gellant has been disclosed in some documents such as Japanese application 05/228915 and U.S. Pat. No. 5,744,130.

In WO 97/11678 to Helene Curtis, Inc, there is described the use of lanosterol as a gellant to make soft gels, sometimes in conjunction with a starch hydrolyzate derivative for antiperspirant compositions.

In WO 98/34588 to Lancaster Group GmbH, there is described the use of lanosterol as a gellant for oil-based cosmetic compositions, containing a cosmetic active material, of which one listed material is a deodorant, though not exemplified.

Antiperspirant emulsion sticks without any material identified as a structurant have been disclosed in U.S. Pat. Nos. 4,673,570, 4,948,578 and 5,587,153.

Cosmetic compositions other than antiperspirants which take the form of structured liquids have been disclosed, for example in U.S. Pat. No. 3,969,087, which disclosed the use of N-acylamino acids and derivatives thereof as gelling agents, and in U.S. Pat. No. 5,486,566 which utilised 12-hydroxy stearic acid.

SUMMARY OF THE INVENTION

It is an object of the present invention to provide thickened or structured cosmetic compositions, especially but not exclusively antiperspirant compositions, in which a liquid carrier material is thickened or structured using a structuring agent or mixture which is or which includes a structuring compound different from those mentioned above. A further object of the invention is to provide a structurant or structurant mixture which can have superior properties to at least some of the structurants which have been used previously.

A further object of at least some forms of the invention is to provide compositions which exhibit low visible deposits when applied. Such compositions may also be somewhat translucent before they are applied to skin.

According to a first aspect of the present invention there is provided a composition of matter suitable for cosmetic use having a continuous phase which comprises water-immiscible liquid and a structurant therein which consists of or includes at least one compound of the general formula (I):

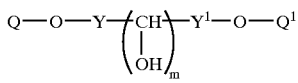
(I)

in which Y and $Y^1$ are independently $-CH_2-$ or $>CO$ Q and $Q^1$ are each a hydrocarbyl group of at least 6 carbon atoms and m is from 2 to 4, preferably 2.

Preferably the group Q and $Q^1$ are groups of the formula

where n has a value of 0 to 10.

The structurant may consist of a single compound within the general formula above, or a mixture of such compounds. Alternatively the structurant may be one or more compounds within the general formula above, mixed with another structurant material or mixture.

The structurant functions to thicken the water-immiscible liquid and when used in a sufficient amount, which is likely to be not over 15% of the total composition, is able to structure this liquid into a gel with sufficient rigidity to sustain its own shape. Lesser amounts would give thickening but without sufficient rigidity to sustain shape.

We have observed that compounds as above used as a structurant in this invention form fibres or strands within the liquid phase.

Without being bound to any specific theory or explanation, we believe that upon gel formulation a network of such fibres is formed which extends throughout the liquid phase. Upon heating the gel to the gel melting temperature, the strands of structurant dissolve and the liquid phase becomes more mobile.

We have also discovered that at least some of the structurant compounds within the general formula above form some very small particles, apparently spheroidal bundles of densely packed fibres, in addition to a network of interconnected fibres.

A scanning electron micrograph of such a composition generally shows a network of fibres substantially less than 1 micron in diameter, which display extensive intersection. In places distributed within this network it is seen that the fibres are densely packed in a circular shape. These spheroidal bundles of fibres have a diameter much larger than the diameter of individual fibres and can also be seen in optical micrographs. They have a diameter within a range from 1 to 40 microns, usually from 2 to 40 microns.

The presence of these spheroidal bundles in addition to a network of interconnected fibres improves the aesthetic qualities of a gelled composition giving it a very smooth feel when applied to the skin.

Consequently, in a second aspect this invention provides a composition of matter suitable for cosmetic use, having a continuous phase which comprises water-immiscible liquid and a structurant therein which forms both a network of interconnected fibres which extends throughout the liquid phase, and a plurality of bundles of more densely packed fibres distributed within the said network.

The water-immiscible liquid used in this invention will frequently function as a carrier for an active ingredient.

In order to promote good sensory properties at the time of use it is preferred to include silicone oil in the water-immiscible carrier liquid. The amount of silicone oil may be at least 10% by weight of the composition and/or at least 40% by weight of the water-immiscible carrier liquid.

Ethanol gives a cooling effect on application to skin, because it is very volatile. It is preferred that the content of ethanol or any monohydric alcohol with a vapour pressure above 1.3 kPa (10 mmHg) is not over 15% better not over 8% by weight of the composition.

As will be explained in more detail below, the structured water-immiscible carrier liquid may be the continuous phase of a composition with a dispersed second phase, either an emulsion or a suspension of particulate solid. Such a solid may be a particulate antiperspirant active. A disperse phase may be a solution of antiperspirant active in water or other hydrophilic solvent.

Further advantages of preferred structurant materials of this invention are that they do not require high processing temperatures and that they are chemically stable, both during processing and in the resultant compositions. The avoidance of high processing temperatures can be especially valuable when the composition contains some water or other volatile constituent.

A composition of this invention will generally be marketed in a container by means of which it can be applied at time of use. This container may be of conventional type.

Another aspect of the invention therefore provides a cosmetic product comprising a dispensing container having at least one aperture for delivery of the contents of the container, means for urging the contents of the container to the said aperture or apertures, and a composition of the first or second aspect of the invention in the container.

The compositions of this invention can be produced by conventional processes for making suspension or emulsion solids or soft-solids.

Thus, according to a fourth aspect of the present invention there is provided a process for the production of a cosmetic composition comprising, not necessarily in any order, the steps of incorporating into a water-immiscible liquid a structurant which consists of or includes one or more compounds of the general formula (I) set out above and/or which is a structurant able to form both a network of fibres and more densely packed bundles of fibres as in the second aspect of this invention.

if required, mixing the liquid with a solid or a disperse liquid phase to be suspended therein, heating the liquid or a mixture containing it to an elevated temperature at which the structurant is soluble in the water-immiscible liquid, followed by introducing the mixture into a mould which preferably is a dispensing container, and then cooling or permitting the mixture to cool to a temperature at which it is thickened or solidified.

A suspended solid may be an antiperspirant active and a disperse phase may be a solution of such an active in a hydrophilic or polar solvent.

According to yet another aspect of the present invention, there is provided a method for preventing or reducing perspiration on human skin comprising topically applying to the skin a composition comprising an antiperspirant active, a water-immiscible liquid carrier and a structurant which consists of or includes at least one compound within the general formula (I) set out above and/or which is a structurant able to form both a network of fibres and more densely packed bundles of fibres as in the second aspect of this invention.

DETAILED DESCRIPTION AND EMBODIMENTS

As mentioned above, the invention requires a structurant compound within a water-immiscible liquid phase. Other materials may also be present depending on the nature of the composition. The various materials will now be discussed by turn and preferred features and possibilities will be indicated.

As mentioned earlier, the structurant compounds of the first aspect of this invention have the following general structure (I):

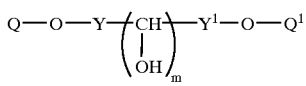

It is preferred that m is 2 so that the structurant compounds comply with a general formula:

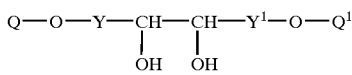

The groups Y and $Y^1$ will usually be identical, i.e. both m methylene or both carbonyl. The groups Q and $Q^1$ may not be the same but often will be identical to each other.

If m is 2 and Y and $Y^1$ are methylene groups, the compound is a derivative of threitol, which is 1,2,3,4-tetrahydroxybutane, while if m is 2 and Y and $Y^1$ are carbonyl groups, the compound is a diester of tartaric acid, which is 2,3-dihydroxybutane-1,4-dioic acid.

It is preferred that each group Q and $Q^1$ contains an aromatic nucleus which may be phenyl or, less preferably, some other aromatic group. Thus Q and $Q^1$ may be groups of the formula

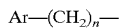

where Ar denotes an aromatic nucleus, notably phenyl or substituted phenyl and n is from 0 to 10.

An aromatic nucleus (Ar) is preferably unsubstituted or substituted with one or more substituents selected from alkyl, alkyloxy, hydroxy, halogen or nitro.

One substituent may be an alkyl or alkyloxy group with a long alkyl chain. Thus a formula for preferred structurants of this invention can be given as

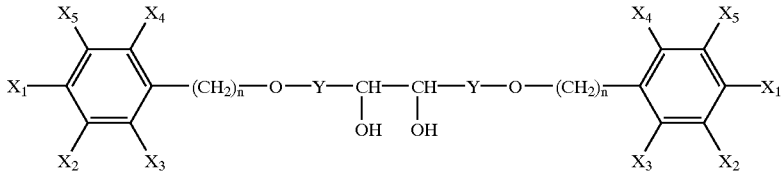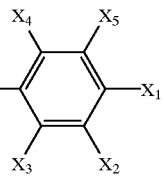

where
n=0 to 10, preferably 0 to 3, more preferably 1, 2 or 3;
Y=—$CH_2$— or >C=O $X_1$=H, Cl, Br, F, OH, $NO_2$, O—R, or R, where R is an aliphatic hydrocarbon chain with 1 to 18 carbon atoms.

$X_2$ to $X_5$ are each independently H, Cl, Br, F, OH, $NO_2$, $OCH_3$, or $CH_3$ In these formulae above, the central carbon atoms which bear hydroxy groups are chiral centres. Thus if m=2, Y and $Y^1$ are the same and Q and $Q^1$ are the same, the compounds will exist as R,R and S,S optically active forms as well as an optically inactive R,S form.

We may prefer to use the optically active R,R or S,S forms or a mixture of the two—which may be a racemic mixture.

Compounds within the general formulae are available commercially. Also, syntheses of these, compounds have been given in scientific literature where the compounds were being used as intermediates for purposes not related to the present invention. Thus syntheses of threitol derivatives can be found in: Kataky et al, J. Chem Soc Perkin Trans vol 2 page 321 [1990] Tamoto et al, Tetrahedron Vol 40 page 4617 [1984], and Curtis et al, J. C. S. Perkin I Vol 15 page 1756 [1977]. Preparations of tartrate esters are found at: Hu et al J. Am. Chem. Soc. Vol 118, 4550 [1996] and Bishop et al J. Org Chem Vol56 5079 [1991].

The structurant used in this invention may contain a mixture of compounds within the general formula (I) or a preferred formula given above, or may be a single compound, possibly as a mixture of its optically active forms.

The amount of structurant in a composition of this invention is likely to be from 0.1 or 0.5 to 15% by weight of the whole composition and preferably from 0.5 up to 8% or 10%, probably from 1 to 8%. If the composition is an emulsion with a separate disperse phase, the amount of structurant is likely to be from 0.5 to 20% or even 25% by weight of the continuous phase, more likely from 1% to 15% of this phase.

If the structurant is one or more compounds within the general formula (I) mixed with one or more other compounds which also act as structurants, the total amount of the compounds of this invention i.e. compounds within the general formula (I) is still likely to be within the weight ranges above, preferably from 0.5% to 8% or 10% of the composition.

The compound(s) within the general formula need not be the majority of the structurant but are likely to be from 20% to 100% of the structurant.

Carrier Liquid

The water-immiscible carrier liquid comprise one or a mixture of materials which are relatively hydrophobic so as to be immiscible in water. Some hydrophilic liquid may be included in the carrier, provided the overall carrier liquid mixture is immiscible with water. It will generally be desired that this carrier is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant –O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier may contain from 0 to 100% by weight of one or more liquid silicones. Preferably, there is sufficient liquid silicone to provide at least 10%, better at least 15%, by weight of the whole composition. If silicone oil is used, volatile silicone preferably constitutes from 20 to 100% of the weight of the carrier liquid. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers include liquid aliphatic or aromatic esters. These may well be used as only part of the liquid carrier, e.g. not above 20%, or even not over 10% by weight of the water-immiscible liquid carrier.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid carrier, but it is preferred that silicone oil is present and that the amount of silicon-free constituents preferably constitutes up to 50 or 60% and in many instances from 20 to 60% by weight of the carrier liquid.

Liquid Disperse Phase

If the composition is an emulsion, in which the structurant acts to thicken (and usually to gel) the continuous phase, the emulsion will contain a more polar disperse phase. The disperse phase may be a solution of an active ingredient.

The hydrophilic disperse phase in an emulsion normally comprises water as solvent and can comprise one or more water soluble or water miscible liquids in addition to or replacement for water. The proportion of water in an emulsion according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with high proportion of disperse phase, i.e. from 65 to 85% disperse phase, may also be advantageous. They can give good hardness even though the structurant in the continuous phase may be only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. $C_{16}$ to $C_{18}$ alcohols ethoxylated with 10 to 25 ethylene oxide residues) and PEG-15-25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPH™, Span™, Tween™, SF1228, DC3225C and Q2-5200.

Antiperspirant Actives

If the composition is an antiperspirant, it will contain an antiperspirant active. Antiperspirant actives, are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the aqueous disperse phase, particularly from 10% or 20% up to 55% or 60% of that phase.

Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 1 μm.

Second Structurant

As already indicated above a second structurant material may be present, possibly in an amount equal to, or more than, the quantity of structurant compound(s) of the general formula (I) given above. A second structurant may or may not be one or more compounds which, also form fibres and thereby gel or thicken a composition.

A second structurant can be non-polymeric or polymeric. Solid linear fatty alcohols may be included but are not preferred. Non-polymeric structurants, sometimes referred to as gellants, can be selected from fatty acids or salts thereof, such as stearic acid or sodium stearate or 12-hydroxy stearic acid. Other suitable gellants can comprise hydrocarbon waxes, ester waxes such as are contained within beeswax, silicone waxes and dibenzylidene alditols, e.g. dibenzylidene sorbitol. Further suitable gellants can comprise lanosterol, a mixture of β-sitosterol, campesterol, or cholesterol with oryzanol, as disclosed in our co-pending UK patent application 9908208.3 esterified cellobiose as disclosed in our co-pending UK patent application 9908202.6, selected N-acylamino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N' dialkylsuccinamides, e.g. dodecyl N,N'-dibutylsuccinamide.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, polyacrylamides, polyacrylates or polyalkylene oxides may be used to structure or thicken this aqueous phase.

One category of polymer which may be employed as a second structurant for the continuous phase is a polysaccharide esterified with monocarboxylic acid containing at least 8 carbon atoms.

Preferred in this category is a dextrin fatty acid ester having the formula

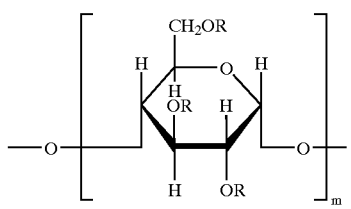

wherein each R group, individually, is a hydrogen or an acyl group of up to 22 carbon atoms, provided that at least one R group per glucose unit is an acyl group of 8 to 22 carbon atoms, and m has a value from about 20 to 30. The dextrin fatty acid ester can be a partial ester, i.e. at least one R group is hydrogen. Another possibility is that the dextrin can be completely esterified with $C_8$ to $C_{22}$ acyl groups, i.e. every R group is a $C_8$–$C_{22}$ acyl group. In preferred embodiments, the degree of substitution with an R group which is a $C_8$–$C_{22}$ alkyl group is at least 2 (i.e., at least two R groups are $C_8$–$C_{22}$ acyl groups). A further possibility would be that some R groups are acyl groups of less than 8 carbon atoms while some R groups (at least one per glucose residue, preferably at least two) is a $C_8$ to $C_{22}$ acyl group.

The $C_8$–$C_{22}$ fatty acids that provide acyl groups can be saturated or unsaturated acids, and include, for example, capric acid, pelargonic acid, caprylic acid, undecylic acid, undecylenic acid, lauric acid, myristic acid, pentadecylic acid, palmitic acid, heptadecylic acid, stearic acid, nonadecanoic acid, arachidic acid, oleic acid, linoleic acid, linolenic acid, similar acids, and mixtures thereof. Dextrin fatty acid esters are disclosed in Mori et al U.S. Pat. No. 4,780,145, incorporated herein by reference, and some of them are available under the trade name RHEOPEARL from Chiba Flour Milling Co., Ltd., Japan. An example of a dextrin fatty acid ester is dextrin palmitate, available commercially as RHEOPEARL KL and RHEOPEARL FL, for example, from Chiba Flour Milling Co., Ltd. Other examples of esters of $C_8$–$C_{22}$ carboxylic acids are dextrin behenate, dextrin laurate, dextrin myristate, dextrin stearate, and mixtures thereof.

Inorganic thickening agents such as fine particle size silicas could possibly be included in compositions of this invention but are not a preferred choice.

Optional Ingredients

Optional ingredients in compositions of this invention can include disinfectants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. Yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test. of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Texture Analyser

The hardness of either a firm stick or a softer solid can be measured by using a texture analyser. This test apparatus can move a blunt probe into or out from a sample at a controlled speed and at the same time measure the applied force. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the Texture Analyser's 5 kg load cell such that it could be used for indenting a sample placed beneath it on the base plate of the instrument. After positioning the, sample, the sphere position was adjusted until it was just above the sample surface. Texture Expert Exceed software was used to generate the subsequent motion profile used in the test method. This profile initially indented the sphere into the sample at an indentation speed of 0.05 mm/s until a designated force was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

Suitable samples for measurement were either contained in stick barrels, which had a screw mechanism, or in 15 ml glass jars. For the barrel samples, the stick was wound up until it protruded above the edges of the barrel and then a knife was used to skim the top of the barrel in such a way as to leave a flat uniform surface. The stick was then pushed back into the barrel as far as possible to minimise any mechanical interference resulting from the compliance of the screw mechanism in the pack. Two indents were generally made either side of the screw. The samples in the 15 ml jars needed no surface preparation but only had enough surface area for a single indentation test to be performed.

The data associated with each test were manipulated using standard spreadsheet software and used to calculate the hardness, H, using the following equation:

$$H[N/mm^2] = \frac{F_{max}[N]}{A_p [mm^2]}$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop Instron Universal Testing Machine (Model 5566) fitted with a 10 N load cell, and the data analysis performed in the same way.

For a stick composition the measured hardness will generally be from 0.03 to 1.0 Newton/mm². Frequently the hardness will be from 0.03 up to 0.35 Newton/mm².

iii) Deposition and Whiteness of Deposit

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions and then measures the mean level of white deposits using image analysis.

The substrates used were a: 12×28 cm strip of grey abrasive paper (3M™ P800 WetorDry™ Carborundum paper)

b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed.

Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

Preparation

Compositions of this invention can be produced by conventional processes for making suspension or emulsion solids or soft-solids. Such processes involve forming a heated mixture of the composition at a temperature which is sufficiently elevated that all the structurant dissolves, pouring that mixture into a mould, which may take the form of a dispensing container, and then cooling the mixture whereupon the structurant solidifies into a network of interconnected fibres extending through the water-immiscible liquid phase.

A convenient process sequence for a-composition which is a suspension comprises first forming a solution of the structurant in the water-immiscible liquid. This is normally carried out by agitating the mixture at a temperature sufficiently high that all the structurant dissolves (the dissolution temperature) such as a temperature in a range from 50 to 120° C. Thereafter the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

In a suitable procedure for making emulsion formulations, a solution of the structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary; antiperspirant actives can sometime be supplied. in aqueous solution which can be utilised as is). If possible, this solution of antiperspirant active which will become the disperse phase is preferably heated to a temperature similar to that of the continuous phase with structurant therein, but without exceeding the boiling point of the solution, and then mixed with the continuous phase. Alternatively, the solution is introduced at a rate which maintains the temperature of the mixture. If it is necessary to work at a temperature above the boiling temperature of the disperse phase, or at a temperature where evaporation from this phase is significant, a pressurised apparatus could be used to allow a higher temperature to be reached. With the structurant materials of this invention this is usually unnecessary. After two phases are mixed, the resulting mixture is filled into dispensing containers, typically at a temperature 5 to 30° C. above the setting temperature of the composition, and allowed to cool as described above for suspension sticks.

EXAMPLES

The examples below were prepared using a number of materials set out with their proprietary names in the following list. All temperature are in degrees Celsius.

1) Volatile cyclic silicones (cyclomethicones) DC 245 and DC 345 (Dow Corning)
2) Non-volatile silicone fluids DC 556 and DC 710 (Dow Corning)
3) Polydecene (Silkflo 364NF from Albemarle)
4) Isostearyl Alcohol (abbreviated to ISA-Prisorine 3515 from Unichema)
5) C12-15 alkyl benzoate (Finsolv TN from Fintex)
6) Mineral Oil (Sirius M70 from Dalton)
7) Isopropyl myristate (abbreviated to IPM-Estol 1514 from Unichema)
8) Cetyl dimethicone copolyol (Abil EM90 emulsifier from Th. Goldschmidt)
9) Al/Zr Tetrachlorohydrex glycine complex (AZAG-7167 from Summit)
10) 50% aqueous solution of Al/Zr pentachlorohydrate (Zirkonal 50 from Giulini)
11) (R,R) -1,4-Di-O-Benzyl-D-Threitol (Sigma Aldrich)

12) (S,S) -1,4-Di-O-Benzyl-D-Threitol (Sigma Aldrich)
13) (R,R) -1,4-chlorobenzyl-D-Threitol (Sigma Aldrich)
14) (S,S) -1,4-chlorobenzyl-D-Threitol (Sigma Aldrich)
15) Dibenzyl-L-Tartrate: (Sigma Aldrich)
16) N-lauryl-L-glutamic acid di-n-butylamide (GP1 from Ajinomoto)
17) β-sitosterol (available as Ultrasitosterol from Kaukas)
18) γ-oryzanol (from Jan Dekker (UK) Ltd)
19) Lanosterol (from Croda Chemicals Ltd)
20) Dextrin palmitate (Rheopearl KL from Chiba Flour Milling Co)
21) Octyldodecanol (Eutanol G from Henkel/Cognis)
22) 12-hydroxystearic acid (from CasChem)
23) Talc (Suprafino A from Cyprus Minerals)
24) 40% aqueous solution of Al/Zr pentachlorohydrate (Rezal 67 from Reheis)

Example 1

Several structurant compounds of this invention were used to gel various water-immiscible liquids and mixtures of liquids. The procedure was as follows:

The structurant compound and the liquid (e.g. 0.5 grams structurant and 9.5 grams of the liquid or other proportions to give a total of 10 grams) were weighed directly into a 15 gram or 30 gram glass jar. A small magnetic follower was placed in the jar which was then. placed on a hot plate. It was stirred and heated until all of the structurant compound had dissolved in the liquid. This "dissolution temperature" was noted. The jar was then removed from the hot plate, the stirrer was removed from the hot liquid in the jar. A thermometer was placed in the liquid and the contents of the jar were then left undisturbed to cool. The gelling temperature, i.e. the temperature at which the contents gelled, was noted. Some clouding of the compositions was observed during cooling before gelation took place. This is attributed to the formation of spheroidal bundles of structuring fibres, discussed above. The jar was left to stand for 24 hours and then the contents of the jar were inspected visually, pressed with a probe and classified qualitatively according to their appearance as a soft, medium or hard gel. The clarity or otherwise of the gel was noted.

The following tables show the water-immiscible liquids which were used, the percentage of structurant compound used to gel the liquid, the dissolution temperature, the gelling temperature and the visual appearance of the gel.

Gelling Studies with 5% of
(R,R)-1,4-Di-O-Benzyl-D-Threitol

| Liquid | wt % gellant | Diss. Temp ° C. | Gel Temp ° C. | Visual Appearance of Gel |
|---|---|---|---|---|
| Estol 1514 | 5 | 45 | 20 | Medium, translucent |
| DC 345 | 5 | 105 | 20 | Soft opaque |
| DC 556 | 5 | 50 | 20 | Hard opaque |
| Silkflo 364NF | 5 | 115 | 20 | Hard opaque |
| Sirius M70 | 5 | 95 | 20 | Medium opaque |
| DC 345:Finsolv TN 50:50 | 5 | 50 | 20 | Hard opaque |
| DC 345:Finsolv TN 80:20 | 5 | 60 | 29 | Hard opaque |

Gelling Studies with 5% of
(S,S)-1,4-Di-O-Benzyl-D-Threitol

| Liquid | wt % gellant | Diss. Temp ° C. | Gel Temp ° C. | Visual Appearance of Gel |
|---|---|---|---|---|
| Finsolv TN | 5 | 40 | 20 | Opaque paste |
| DC 345 | 5 | 56 | 20 | Soft opaque |
| DC 556 | 5 | 87 | 28 | Hard opaque |
| Sirius M70 | 5 | 110 | 20 | Opaque hard gel formed overnight |
| DC 345:Finsolv TN 50:50 | 5 | 55 | 20 | Opaque hard gel formed after 48 hours |
| DC 345:Finsolv TN 80:20 | 5 | 120 | 33 | Soft opaque |

Gelling Studies with varying amounts of
(R,R)-1,4-Di-O-(4-chlorobenzyl)-D-Threitol

| Liquid | wt % gellant | Diss. Temp ° C. | Gel Temp ° C. | Visual Appearance of Gel |
|---|---|---|---|---|
| DC 345 | 2.5 | n/d | 20 | Soft opaque |
|  | 5 | 125 | 29 | Soft opaque |
| DC556 | 2.5 | n/d | 24 | Very soft opaque |
|  | 5 | 129 | 20 | Medium opaque gel after 30 minutes |
| Silkflo 364 NF | 2.5 | n/d | 20 | Medium opaque |
|  | 5 | 130 | 23 | Medium opaque |
| DC 345:Finsolv TN 40:60 | 5 | 71 | 20 | Hard translucent |
| DC 345:Finsolv TN 50:50 | 5 | n/d | 20 | Hard translucent/opaque |
| DC 345:Finsolv TN 60:40 | 5 | 70 | 20 | Medium opaque |
| DC 345:Finsolv TN 70:30 | 5 | 69 | 20 | Medium opaque |
| DC 345:Finsolv TN 80:20 | 1.0 | n/d | 27 | Soft opaque |
|  | 1.3 | n/d | 26 | Medium opaque |
|  | 1.7 | n/d | 30 | Hard opaque |
|  | 2.5 | n/d | 34 | Hard opaque |
|  | 5 | 87 | 28 | Hard opaque |

Gelling Studies with 5% of
(S,S)-1,4-Bis-O-(4-Chlorobenzyl)-D-Threitol

| Liquid | wt % gellant | Diss. Temp ° C. | Gel Temp ° C. | Visual Appearance of Gel |
|---|---|---|---|---|
| Finsolv TN | 5 | 47 | 20 | Soft opaque |
| DC 345 | 5 | 63 | 48 | Soft opaque |
| DC 556 | 5 | 82 | 50 | Very hard opaque |
| Silkflo 364 NF | 5 | 62 | 39 | Medium opaque |
| DC 345:Finsolv TN 80:20 | 5 | 65 | 46 | Hard opaque |

Gelling Studies with 5% of a 1:1 mixture of (R,R)-1,4-Bis-O-(4-Chlorobenzyl)-D-Threitol and (S,S)-1,4-Bis-O-(4-Chlorobenzyl)-D-Threitol

| Liquid | wt % gellant | Diss. Temp ° C. | Gel Temp ° C. | Visual Appearance of Gel |
|---|---|---|---|---|
| DC 556 | 5% total | 114 | 20 | Medium opaque |
| Silkflo 364 NF | 5% total | 105 | 20 | Opaque hard |
| Sirius M70 | 5% total | 100 | 20 | Medium opaque |
| DC 345:Finsolv TN 80:20 | 5% total | 75 | 20 | Hard opaque |

Gelling Studies with 5% of Dibenzyl-L-Tartrate

| Liquid | wt % gellant | Diss. Temp ° C. | Gel Temp ° C. | Visual Appearance of Gel |
|---|---|---|---|---|
| Finsolv TN | 5 | 55 | 20 | Opaque hard |
| Estol 1514 | 5 | 56 | 20 | Opaque hard |
| Prisorine 3515 | 5 | 87 | 20 | Opaque soft |
| DC 556 | 5 | 115 | 32 | Opaque hard |
| Silkflo 364 NF | 5 | 65 | 20 | Opaque soft |
| Sirius M70 | 5 | 60 | 20 | Opaque medium |
| DC 345:Finsolv TN 50:50 | 5 | 70 | 33 | Opaque hard |
| DC 345:Finsolv TN 80:20 | 5 | 65 | 52 | Opaque soft |

Gelling studies with varying amounts of a 1:1 mixture of (R,R)-1,4-Bis-O-(4-Chlorobenzyl)-D-Threitol and N-lauryl-L-glutamic acid di-n-butylamide (GP-1)

| Liquid | wt % total gellant | Diss Temp ° C. | Gel Temp ° C. | Visual Appearance of Gel |
|---|---|---|---|---|
| DC 345:Finsolv TN 80:20 | 1 | n/d | 76 | Soft opaque |
|  | 1.4 | n/d | 76 | Medium opaque |
|  | 2 | n/d | 80 | Medium opaque |
|  | 4 | 123 | n/d | Medium opaque |

Some of the gels made in this example were studied by scanning electron microscope. The micrographs generally showed a network of fibres substantially less than 1 micron in diameter, which displayed extensive intersection.

In places distributed within this network the fibres were densely packed in a circular shape. These spherical bundles of fibres had a diameter much larger than the diameter of individual fibres and could also be seen in optical micrographs. They had diameters within a range from 1 to 40 microns.

Example 2

Antiperspirant suspension sticks were prepared using a water-immiscible liquid or a mixture of water-immiscible liquids, an antiperspirant active and a structurant compound. In all cases the procedure was as follows: the liquid or mixture of liquids, together with the structurant compound was heated to a temperature at which the structurant compound dissolved. During this heating the liquid was mixed gently using a Silverson mixer. The mixture was allowed to cool to 70° C. The particulate antiperspirant active was added to this solution. At this stage the mixture was poured into antiperspirant stick barrels and left to cool without further disturbance until the formulation had solidified.

The resulting sticks were evaluated after at least 24 hours at ambient laboratory temperature. In all cases the appearance of the stick was noted, the hardness was determined by penetrometer and texture analyser, and tests of deposition and whiteness of the resulting deposit were carried out using the procedures described earlier.

The formulations which were prepared and the properties of the resulting sticks are set out in the table below. The testing of hardness and whiteness of deposit was also carried out with a commercial white solid stick (CWS) structured with 15% stearyl alcohol and 3% castor wax, these percentages being by weight of its whole composition.

Suspension Sticks

| Formulation No: | 2.1 | 2.2 | 2.3 | 2.4 | CWS |
|---|---|---|---|---|---|
| (R,R)-1,4-Di-O-Benzyl-D-Threitol | — | — | 5% | 5% | — |
| (R,R)-1,4-Bis-O-(4-Chlorobenzyl)-D-Threitol | 5% | 5% | — | — | — |
| DC 345 | 56.8% | 56.8% | 56.8% | 56.8% | — |
| Finsolv TN | 14.2% | — | 14.2% | — | — |
| Silkflo NF | — | 14.2% | — | 14.2% | — |
| Summit Q5-7167 | 24% | 24% | 24% | 24% | — |
| Properties |  |  |  |  |  |
| Hardness N/mm$^2$ | 0.105 | 0.108 | 0.048 | 0.057 | 0.24 |
| Whiteness on grey paper 24 hours after deposition | 38 | 54 | 36 | 35 | 118 |
| Whiteness on black wool 24 hours after deposition | n/d | 37 | 23 | 11 | 186 |

All of the sticks 2.1 to 2.4 were considered to have a gentle "silky" aesthetic feel, better than the conventional white stick, when applied to skin. Although these sticks had lower hardness than the conventional white stick they were all firm enough to be applied to skin without difficulty.

Further suspension sticks were made in which a mixture of (R,R)-1,4-Di-O-Benzyl-D-Threitol and a second structurant were employed as the structuring system. Preparation was essentially as described above except that the antiperspirant active was added at a higher temperature between 75° C. and 100° C. Formulations and properties are given in the table below.

Suspension Sticks

| Formulation No: | 2.5 | 2.6 | 2.7 | 2.8 |
|---|---|---|---|---|
| (R,R)-1,4-Di-O-Benzyl-D-Threitol | 7% | — | — | — |
| (R,R)-1,4-Bis-O-(4-Chlorobenzyl)-D-Threitol | — | 3% | 3% | 3% |
| GP-1 | 2% | — | — | — |
| β Sitosterol | — | 2% | — | — |
| Oryzanol | — | 2% | — | — |
| Lanosterol | — | — | 2% | 2% |
| DC 345 | 53.6% | 48.3% | 56.8% | 55.2% |
| Finsolv TN | 13.4% | — | — | — |

-continued

| Suspension Sticks | | | | |
|---|---|---|---|---|
| Formulation No: | 2.5 | 2.6 | 2.7 | 2.8 |
| Silkflo 364 NF | — | 6.9% | — | — |
| Isostearyl alcohol | — | 13.8% | — | — |
| DC 556 | — | — | 14.2% | 13.8% |
| Summit Q5-7167 | 24% | 24% | 24% | 24% |
| Properties | | | | |
| Hardness N/mm$^2$ | 0.135 | 0.178 | 0.062 | 0.098 |
| Whiteness on grey paper 24 hours after deposition | 32 | 41 | 41 | 39 |
| Whiteness on black wool 24 hours after deposition | 23 | n/d | 32 | 23 |

The sticks (2.5 and 2.6) made with GP-1 and β-Sitosterol/Oryzanol were generally harder than the sticks made without a second structurant, but they still had a soft silky feel when applied to the skin. The sticks (2.7 and 2.8) made with lanosterol were a little softer than these, but still had a good skin feel (although not as good as those made as 2.1 to 2.6).

Example 3

Opaque emulsion sticks were prepared with formulations as set out in the tables below.

To prepare these sticks, the structurant compound was mixed with the carrier liquid including the cetyl dimethicone copolyol which functioned as an emulsifier (silicone surfactant) and the mixture was heated with gentle stirring until the structurant dissolved. The temperature was then adjusted to about 90° C.

The disperse phase (also referred to as internal phase) was an aluminium zirconium active dissolved in water and slightly diluted with additional water. This disperse phase was pre-heated to about 90° C., i.e. the same temperature as the organic liquid mixture containing the structurant and added slowly to them over a period of one minute while mixing with a Silverson mixer. After addition was complete the formulation was mixed at higher speed for five minutes. After this the mixture was poured into stick barrels and allowed to cool undisturbed to ambient laboratory temperature. The sticks were tested by penetrometer, by texture analyser and for whiteness of deposits, in each instance by the test procedures given earlier. All of the sticks were opaque.

| Emulsion Sticks | | |
|---|---|---|
| Formulation No | 3.1 | 3.2 |
| (R,R)-1,4-Di-O-Benzyl-D-Threitol | — | 7% |
| (R,R)-1,4-Bis-O-(4-Chlorobenzyl)-D-Threitol | 5% | — |
| DC 345 | 35% | 33.4% |
| Finsolv TN | 9% | 8.6% |
| Abil EM 90 | 1% | 1% |
| Zirkonal 50 | 40% | 40% |
| Water | 10% | 10% |
| Properties | | |
| Hardness N/mm$^2$ | 0.091 | 0.114 |
| Whiteness on grey paper 24 hours after deposition | n/d | 34 |
| Whiteness on black wool 24 hours after deposition | n/d | 13 |

These stick were found to have a gentle, silky feel when applied to skin.

Example 4

Further antiperspirant suspension sticks were prepared as in Example 2. Their formulations and properties are given in the table below. Three of the four formulations include a second, non-polymeric structurant which was incorporated during the initial stage of heating in the mixture of liquids until all structurant had dissolved.

| Suspension Sticks with R,R-1,4-Di-O-Benzyl-D-Threitol | | | | |
|---|---|---|---|---|
| Formulation No: | 4.1 | 4.2 | 4.3 | 4.4 |
| (R,R)-1,4-Di-O-Benzyl-D-Threitol | 7% | 5% | 5% | 4% |
| GP-1 | | 2% | 2% | |
| 12-hydroxystearic acid | | | | 3% |
| DC 245 | 55.2% | 55.2% | 55.2% | 55.2% |
| Finsolv TN | | 13.8% | | |
| Eutanol G | 13.8% | | 13.8% | 13.8% |
| Summit 7167 (AZAG) | 24% | 24% | 24% | 24% |
| Properties | | | | |
| Penetrometer Hardness (mm) | 7.3 | 4.3 | 5.7 | 6.7 |
| Whiteness on grey paper 24 hours after deposition | 72 | 41 | 36 | 37 |
| Whiteness on black wool 24 hours after deposition | 102 | 41 | 50 | 93 |

All of these sticks were found to give a gentle silky feel when applied to skin.

Example 5

Antiperspirant suspension sticks which incorporate a polymeric second structurant were prepared, one again following the procedure of Example 2. The polymeric second structurant and the threitol derivative were both included in the initial step of heating (in the liquid mixture until they had dissolved. The polymer employed was dextrin palmitate described earlier.

Formulations and properties are set out in the table below.

| Suspension Sticks with R,R-1,4-Di-O-Benzyl-D-Threitol and dextrin palmitate | | | | |
|---|---|---|---|---|
| Formulation No: | 5.1 | 5.2 | 5.3 | 5.4 |
| (R,R)-1,4-Di-O-Benzyl-D-Threitol | 5% | 5% | 5% | 5% |
| Dextrin palmitate | 2% | 5% | 2% | 3% |

-continued

Suspension Sticks with R,R-1,4-Di-O-Benzyl-D-Threitol
and dextrin palmitate

| Formulation No: | 5.1 | 5.2 | 5.3 | 5.4 |
|---|---|---|---|---|
| DC 245 | 53.6% | 52.2% | 53.2% | 54.2% |
| Finsolv TN | 13.4% | 13.8% | 13.8% | 13.8% |
| Summit 7167 (AZAG) | 24% | 24% | 24% | 24% |
| Talc | 2% | | | |
| Properties | | | | |
| Penetrometer Hardness (mm) | 8.5 | 6.2 | 5.3 | 6.7 |
| Whiteness on grey paper 24 hours after deposition | 76 | 41 | 52 | 60 |
| Whiteness on black wool 24 hours after deposition | 76 | 41 | 32 | 60 |

All of these sticks were found to give a gentle silky feel when applied to skin.

Example 6

Further opaque emulsion antiperspirant sticks were prepared as in Example 3. One formulation included a second non-polymeric structurant, which was included in the initial step of heating in the carrier liquid.

Formulations and properties are given in the table below.

Emulsion Sticks with R,R-1,4-Di-O-Benzyl-D-Threitol

| Formulation No: | 6.1 | 6.2 | 6.3 |
|---|---|---|---|
| (R,R)-1,4-Di-O-Benzyl-D-Threitol | 5% | 5% | 5% |
| GP-1 | — | — | 1% |
| DC 245 | 34% | 33% | 34% |
| Finsolv TN | 10% | 9% | 9% |
| Talc | — | 2% | — |
| Rezal 67 | 50% | 50% | 50% |
| Abil EM90 | 1% | 1% | 1% |
| Properties | | | |
| Penetrometer Hardness (mm) | 6.4 | 6.3 | 6.8 |
| Whiteness on grey paper 24 hours after deposition | 22 | 52 | 29 |
| Whiteness on black wool 24 hours after deposition | 29 | 54 | 32 |

Example 7

Opaque emulsion antiperspirant sticks were prepared, incorporating dextrin palmitate as a polymeric second structurant. Preparation was by the procedure of Example 3, incorporating both the threitol derivative and the dextrin palmitate in the initial step of heating in the carrier liquid. In one formulation the disperse phase was and aqueous glycerol solution.

Formulations and properties are given in the table below.

Emulsion Sticks with R,R-1,4-Di-O-Benzyl-D-Threitol and dextrin palmitate

| Formulation No: | 7.1 | 7.2 | 7.3 | 7.4 | 7.5 |
|---|---|---|---|---|---|
| (R,R)-1,4-Di-O-Benzyl-D-Threitol | 5% | 5% | 5% | 6% | 6% |

-continued

Emulsion Sticks with R,R-1,4-Di-O-Benzyl-D-Threitol and dextrin palmitate

| Formulation No: | 7.1 | 7.2 | 7.3 | 7.4 | 7.5 |
|---|---|---|---|---|---|
| Dextrin palmitate | 2% | 3% | 4% | 2% | 2% |
| DC 245 | 32% | 32% | 32% | 32% | 32% |
| Finsolv TN | 8% | 9% | 8% | 9% | 9% |
| Talc | 2% | — | — | — | — |
| Rezal 67 | 50% | 50% | 50% | 50% | 48% |
| Abil EM90 | 1% | 1% | 1% | 1% | 1% |
| Glycerol | — | — | — | — | 2% |
| Properties | | | | | |
| Penetrometer Hardness (mm) | 12.1 | 8.9 | 8.8 | 5.3 | n/d |
| Whiteness on grey paper 24 hours after deposition | 33 | 40 | 41 | 39 | 27 |
| Whiteness on black wool 24 hours after deposition | 31 | 32 | 29 | 38 | 20 |

What is claimed is:

1. A composition of matter suitable for cosmetic use comprising a continuous phase which contains a water-immiscible liquid and a structurant therein which comprises at least one structurant compound of the general formula $$Q-O-Y-\left(\underset{OH}{\overset{}{C}H}\right)_m-Y^1-O-Q^1 \tag{I}$$

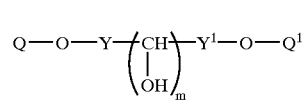

in which Y and $Y^1$ are each independently $-CH_2-$ or $>CO$
Q and $Q^1$ are each independently a hydrocarbyl group of at least 6 carbon atoms, and m is from 2 to 24.

2. A composition according to claim 1 wherein the groups Q and $Q^1$ are groups of the formula $$Ar-(CH_2)_n-$$

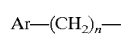

where Ar denotes an aromatic nucleus and n has a value of 0 to 10.

3. A composition according to claim 1 wherein Y and $Y^1$ are the same and m is 2.

4. A composition according to claim 1 wherein Q and $Q^1$ are the same.

5. A composition according to claim 1 wherein said structurant compound is of the formula:

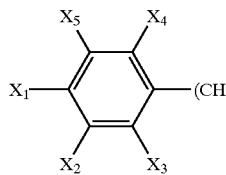 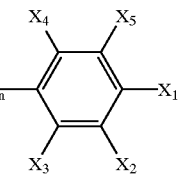

n=0 to 10,
Y=—CH$_2$— or >C=O
X$_1$=H Cl, Br, F, OH, NO$_2$, O—R, or R, and R is an aliphatic hydrocarbon chain with 1 to 18 carbon atoms;
X$_2$=H Cl, Br, F, OH, NO$_2$, O—CH$_3$, or CH$_3$
X$_3$=H Cl, Br, F, OH, NO$_2$, O—CH$_3$, or CH$_3$
X$_4$=H Cl, Br, F, OH, NO$_2$, O—CH$_3$, or CH$_3$
X$_5$=H Cl, Br, F, OH, NO$_2$, O—CH$_3$, or CH$_3$.

6. A composition according to claim 5 where n is 1.

7. A composition according to claim 5 wherein m is 2 and said structurant compound is in an R,R or S,S optically active configuration.

8. A composition according to claim 5 wherein said structurant compound is a racemic mixture.

9. A composition according to claim 1 characterised in that the water-immiscible liquid carrier contains a volatile silicone and optionally a non-volatile silicone and/or a non-silicone hydrophobic organic liquid selected from hydrocarbons, hydrophobic aliphatic esters, aromatic esters and hydrophobic alcohols.

10. A composition according to claim 1 wherein the water-immiscible carrier liquid contains silicone oil in an amount which is at least 10% by weight of the composition.

11. A composition according to claim 1 containing from 0.1 to 15% by weight of the structurant.

12. A composition according to claim 1 which contains not more than 5% by weight of any fatty alcohol which is solid at 20° C.

13. A composition according to claim 1 wherein the composition is an emulsion with a hydrophilic, preferably water-miscible, disperse phase in addition to said water-immiscible liquid continuous phase.

14. A composition according to claim 13 wherein the disperse phase contains a diol or polyol.

15. A composition according to claim 14 wherein the disperse phase contains glycerol, or 1,2-propanediol.

16. A composition according to claim 13 which contains from 0.1% to 10% by weight of a nonionic emulsifier.

17. A composition according to claim 13 which does not contain more than 8% by weight of ethanol or any monohydric alcohol with a vapour pressure above 1.3 kPa at 22° C.

18. A composition according to claim 1 wherein the composition is a suspension with a particulate solid material dispersed in said liquid continuous phase.

19. A composition according to claim 1 which is an antiperspirant composition comprising an antiperspirant active.

20. A composition according to claim 19 wherein the antiperspirant active comprises an aluminium and/or zirconium halohydrate, an activated aluminium and/or zirconium halohydrate, or an aluminium and/or zirconium complex or an activated aluminium and/or zirconium complex.

21. A composition according to claim 1 which is an antiperspirant composition comprising a particulate antiperspirant active in suspension in said water-immiscible immiscible continuous phase.

22. A composition according to claim 13 which is an antiperspirant composition comprising an antiperspirant active dissolved in said disperse phase.

23. A composition according to claim 22 wherein the antiperspirant active comprises a halohydrate or complex in which aluminium and zirconium are both present.

24. A composition according to claim 19 wherein the proportion of antiperspirant active is from 5 to 40% by weight of the composition.

25. A composition according to claim 1 preceding claims which is a firm gel such that hardness measured by texture analyser lies in a range from 0.03 to 1.0 Newton/mm$^2$.

26. A composition of matter suitable for cosmetic use, having a continuous phase which comprises water-immiscible liquid and a structurant therein which forms both a network of interconnected fibres which extends throughout the liquid phase, and a plurality of bundles or more densely packed fibres distributed within the said network.

27. An antiperspirant product comprising a dispensing container having at least one aperture for delivery of the contents of the container, means for urging the contents of the container to the said aperture or apertures, and a composition according to claim 1 accommodated within the container.

28. A product according to claim 27 wherein the composition is in the form of a stick and the container has an open end at which an end portion of the stick of composition is exposed for, use.

29. A process for the production of a composition according to claim 1 comprising, not necessarily in any order, the steps of incorporating into a water-immiscible liquid at least one compound of the general formula (I):

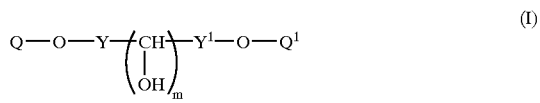

in which Y and Y$^1$ are each independently —CH$_2$— or >CO

Q and Q$^1$ are each independently a hydrocarbyl group of at least 6 carbon atoms and m is from 2 to 4;

if required, mixing the liquid with a solid or a disperse liquid phase to be suspended therein;

heating to an elevated temperature at which the structurant is in solution in the water-immiscible liquid;

followed by cooling or permitting the mixture to cool to a temperature at which it is thickened or solidified.

30. A process according to claim 29 which includes a step of pouring the mixture at elevated temperature into a dispensing container and allowing it to cool therein so as to produce a product according to claim 27.

31. A process according to claim 29 wherein m is 2 and Y and $Y^1$ are the same.

32. A process according to claim 31 wherein Q and $Q^1$ are the same.

33. A method for preventing or reducing perspiration on human skin comprising topically applying to the skin a composition according to claim 19.

* * * * *